United States Patent [19]

Rasp et al.

[11] 4,016,201

[45] Apr. 5, 1977

[54] PROCESS FOR THE PREPARATION OF ACETOXYBUTANOLS

[75] Inventors: Christian Rasp, Cologne; Johann Grolig, Leverkusen, both of Germany

[73] Assignee: Bayer Aktiengesellschaft, Leverkusen, Germany

[22] Filed: June 18, 1975

[21] Appl. No.: 588,077

[30] Foreign Application Priority Data

June 22, 1974 Germany ............................ 2430038

[52] U.S. Cl. .............................. 260/491; 260/635 R
[51] Int. Cl.$^2$ ............................................ C07C 67/28
[58] Field of Search ...................... 260/491, 635 A

[56] References Cited

UNITED STATES PATENTS 3,769,331  10/1973  Kuckertz et al. ................. 260/491

*Primary Examiner*—Vivian Garner
*Attorney, Agent, or Firm*—Burgess, Dinklage & Sprung

[57] ABSTRACT

In the process for the preparation of an acetoxybutanol by hydrogenation of the corresponding acetoxybutyraldehyde in the presence of metals of group VIII of the periodic table, the improvement which comprises carrying out the hydrogenation in the presence of methanol. The rate of reaction is improved by the use of methanol.

3 Claims, No Drawings

PROCESS FOR THE PREPARATION OF ACETOXYBUTANOLS

Application Ser. No. 588,078, filed June 18, 1975; application Ser. No. 588,079 filed June 18, 1975; application Ser. No. 588,080, filed June 18, 1975 which is abandoned; all assigned to the assignee hereof and directed to related subject matter.

BACKGROUND

The present invention relates to a process for the preparation of acetoxybutanols by hydrogenation of acetoxybutyraldehydes.

The acetoxybutanols are valuable starting materials for the preparation of butanediols. Butanediols are industrially used solvents and intermediate products for the preparation of polyurethanes, epoxide resins, polyesters, polyamides and plasticisers. 1,4-butanediol is particularly suitable for the preparation of polyurethanes and thermoplasts (Kirk-Othmer, Encyclopedia of Chemical Technology, 2nd Ed., Vol 10, 672 (1966)). 1,2-Butanediol can be processed to alkyd resins (U.S. Pat. No. 2,965,587); 2-methyl-1,3-propanediol is a valuable starting material for the production of polyesters from which dyeable fibres can be manufactured (French Specification No. 1.303.888).

It is known to convert 2-acetoxybutyraldehyde to the corresponding butanediol by hydrogenation and hydrolysis (U.S. Pat. No. 2,428,760, column 2, lines 50 to 55).

Catalysts based on metals of group VIII of the periodic table are suitable for the preparation of acetoxybutanol from acetoxybutyraldehyde by hydrogenation with hydrogen. For example, the hydrogenation can be carried out with nickel, cobalt or noble metal catalysts, such as palladium. For industrial use of the process it is of interest to achieve a high speed of hydrogenation and practically quantitative conversion of the aldehyde to the alcohol.

THE INVENTION

In accordance with this invention, it has now been found, surprisingly, that the rate of hydrogenation, in the reaction of acetoxybutyraldehydes with hydrogen to give acetoxybutanols, can be increased substantially by carrying out the hydrogenation in the presence of methanol. In general, the addition of methanol in an amount of 1 to 50 per cent by weight is suitable. In a preferred procedure, 5 to 10% by weight of methanol are added to the staring material and the hydrogenation is then carried out in the presence of metals of group VIII of the periodic table, (Mendeleev).

Starting materials which can be used for the hydrogenation are not only the individual isomeric acetoxybutyraldehydes separately, for example 4-acetoxybutyraldehyde, 2-acetoxybutyraldehyde or 3-acetoxy-2-methylpropionaldehyde, but also their mixtures. In particular, it is possible to use the acetoxybutyraldehyde mixtures obtained on reaction of allyl acetate with carbon monoxide and hydrogen in the presence of metal carbonyls. During the hydrogenation, a partial reaction of the methanol with the acetoxybutanol formed, to give butanediol and methyl acetate, can occur. This reaction is no disadvantage and may be a distinct advantage if, for example, the acetoxybutanol is to be converted further to butanediol. In that case the crude hydrogenation mixture can be reacted with further methanol, in the presence of an alkaline catalyst, to give methyl acetate and butanediol. In general, the process according to the invention is carried out as follows:

Acetoxybutyraldehyde (acetoxybutanal) in the liquid phase is treated with hydrogen in the presence of catalysts consisting of metals of group VIII of the periodic table. Possible catalysts are cobalt, nickel, palladium, iron, platinum, rhodium, ruthenium and iridium. The catalysts can be used in a suspended, finely divided form, for example as Raney cobalt, Raney nickel and palladium black. They can also be used in the form of supported catalysts. Suitable supports are aluminium oxide, silicon dioxide, active charcoal, aluminium spinels and aluminium silicates. If a suspended catalyst is used, the catalyst can be separated off mechanically, for example by filtration or centrifuging, after completion of the reaction. The reaction can also be carried out in a trickle phase, the acetoxybutanal/methanol mixture being allowed to trickle, over a fixed catalyst, in a virtually static hydrogen atmosphere. Suitable temperatures for carrying out the hydrogenation are 100°–250° C, for example 150°–200° C. The reaction is advantageously carried out under pressure, for example at a pressure of 5–300 bars, for example 10–200 bars or 50–150 bars. Atmospheric pressure, however, can be used. The catalyst-free reaction product can be used, without further pre-treatment, in further chemical syntheses, for example the further conversion of the acetoxybutanol to butanediol. In the interest of the quality of the butanediol it is important that the hydrogenation of the acetoxybutanal to acetoxybutanol should take place virtually completely, for example with a yield of 99%.

The process according to the invention has the advantage that the rate of hydrogenation can be increased by a factor of 10 or more by adding small amounts of methanol. Accordingly, substantially higher throughputs are achieved with existing equipment.

EXAMPLE 1 (for comparison)

Acetoxybutyraldehyde (a mixture of the three isomers disclosed above) was treated with hydrogen in the presence of 2% by weight of Raney cobalt, at 150° C and 200 bars. The time required to convert 99 % of the acetoxybutyraldehyde to acetoxybutanol by hydrogenation was determined by titrating the residual aldehyde content with hydroxylamine hydrochloride as the reagent. It was found that a reaction time of 300 minutes is needed to reach 99 % conversion of the aldehyde. The following examples illustrate the present invention:

EXAMPLE 2

The procedure in Example 1 was followed except that 5% by weight of methanol were added to the reaction mixture. After a reaction time of 35 minutes, 99% conversion of acetoxybutyraldehyde to acetoxybutanol was reached.

EXAMPLE 3

The procedure in Example 1 was followed except that 10% by weight of methanol were added. After a hydrogenation time of 15 minutes, 99% conversion of acetoxybutyraldehyde to acetoxybutanol was reached.

EXAMPLE 4

The procedure in Example 1 was followed but instead of the acetoxybutyraldehyde isomer mixture, 4-acetoxybutyraldehyde was employed and the hydrogenation was carried out in the presence of 5% by weight of methanol. After a hydrogenation time of 35 minutes, and after filtering off the catalyst and freeing the filtrate from methanol, 4-acetoxybutan-1-ol was obtained in 99% yield.

EXAMPLE 5

The procedure in Example 4 was followed except that 3-acetoxy-2-methylpropionaldehyde was hydrogenated in place of 4-acetoxybutyraldehyde, in the presence of 5% by weight of methanol. After a hydrogenation time of 30 minutes and after working up as described in Example 4, pure 3-acetoxy-2-methylpropan-1-ol was obtained in 99% yield.

The 3-acetoxy-2-methylpropionaldehyde employed in the hydrogenation was prepared as follows:

6 g of iron pentacarbonyl and 20 mg of rhodium trichloride in 200 ml of o-xylene were reacted, whilst stirring, with a $CO/H_2$ mixture in the molar ratio of 1:1 in an autoclave at 170° C for one hour at 300 bars. The temperature was then lowered to 135° C. 200 g of allyl acetate were pumped in over the course of 20 minutes. The pressure was kept at 300 bars by adding $CO/H_2$ mixture. The reaction was carried out at 135° C. 40 minutes after the end of the pumping-in stage, the autoclave was cooled to room temperature and the pressure was released. 99.5% of the allyl acetate employed had reacted. The reaction mixture was fractionally distilled under reduced pressure. A fraction, boiling at 65°–67° C under a pressure of 4 mm Hg, was obtained in an amount of 114 g. It was found, by gas chromatography and nuclear resonance spectroscopy, that the fraction was a single compound, consisting of 3-acetoxy-2-methylpropionaldehyde. Working up by distillation gave first runnings boiling at 57°–59° C at 4.5 mm Hg and consisting of 2-acetoxybutyraldehyde, as well as a fraction, boiling at 80°–81° C under a pressure of 4.5 mm Hg, which consisted of 4-acetoxybutyraldehyde.

What is claimed is:

1. In the process for the preparation of an acetoxybutanol by hydrogenation of the corresponding acetoxybutyraldehyde in the presence of a metal of group VIII of the periodic table, wherein the acetoxybutyraldehyde is at least one of 4-acetoxybutyraldehyde, 2-acetoxybutyraldehyde, and 3-acetoxy-2-methylpropionaldehyde, the improvement which comprises carrying out the hydrogenation in the presence of methanol in an amount of 1 to 50% by weight, relative to acetoxybutyraldehyde employed.

2. Process according to claim 1, characterised in that methanol is used in an amount of 5 to 10% by weight, relative to acetoxybutyraldehyde employed.

3. Process for the preparation of 3-acetoxy-2-methylpropan-1-ol, characterised in that 3-acetoxy-2-methylpropionaldehyde is hydrogenated in the presence of a metal of group VIII of the periodic table and in the presence of methanol in an amount of 1 to 50% by weight, relative to the 3-acetoxy-2-methyl-propionaldehyde employed.

* * * * *